United States Patent
Rothenberg

(10) Patent No.: US 9,437,116 B2
(45) Date of Patent: Sep. 6, 2016

(54) SYSTEM FOR SUBGLOTTAL PRESSURE MEASUREMENT AND DISPLAY DURING SPEECH

(71) Applicant: Martin Rothenberg, Jamesville, NY (US)

(72) Inventor: Martin Rothenberg, Jamesville, NY (US)

( * ) Notice: Subject to any disclaimer, the term of this patent is extended or adjusted under 35 U.S.C. 154(b) by 203 days.

(21) Appl. No.: 13/998,940

(22) Filed: Dec. 24, 2013

(65) Prior Publication Data

US 2015/0181358 A1    Jun. 25, 2015

(51) Int. Cl.
| | |
|---|---|
| *G10L 21/00* | (2013.01) |
| *G09B 19/04* | (2006.01) |
| *A61B 5/00* | (2006.01) |
| *A61B 5/03* | (2006.01) |
| *G10L 17/26* | (2013.01) |

(52) U.S. Cl.
CPC ............... *G09B 19/04* (2013.01); *A61B 5/00* (2013.01); *A61B 5/036* (2013.01); *A61B 5/038* (2013.01); *A61B 5/4803* (2013.01); *G10L 17/26* (2013.01); *G10L 21/00* (2013.01); *H04R 2410/00* (2013.01)

(58) Field of Classification Search
CPC ...... G10L 17/26; G10L 21/00; A61B 5/4803
See application file for complete search history.

(56) References Cited

U.S. PATENT DOCUMENTS

| 3,632,877 A | * | 1/1972 | Gray | 381/54 |
| 4,628,526 A | * | 12/1986 | Germer | 381/57 |
| 2006/0061394 A1 | * | 3/2006 | Hausdorf et al. | 327/58 |

* cited by examiner

*Primary Examiner* — Duc Nguyen
*Assistant Examiner* — Kile Blair

(57) ABSTRACT

A method and device is described for estimating the subglottal air pressure during speech or singing from the intraoral air pressure in essentially real-time by using a type of peak detection and extrapolation means that holds peaks in the low-pass filtered pressure signal for a period of time sufficient to allow their interpretation as real-time subglottal pressure. An electronic circuit suitable for implementing this function is described.

5 Claims, 5 Drawing Sheets

SYSTEM FOR SUBGLOTTAL PRESSURE MEASUREMENT AND DISPLAY DURING SPEECH

CROSS-REFERENCE TO RELATED APPLICATIONS

Figure 1:
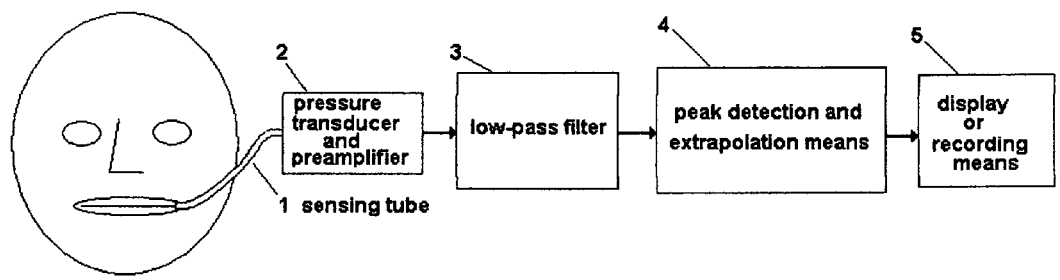

This application claims the benefit of a provisional patent application having the same title filed by the present inventor in January of 2013. There is no serial number available at this time.

BACKGROUND

Prior Art

The following is a tabulation of some prior art that presently appears relevant:

NONPATENT LITERATURE DOCUMENTS

Kitzing, P. & Löfqvist, A. Subglottal and oral air pressures during phonation: Preliminary investigation using a miniature transducer system. *Medical and Biological Engineering* 13: pp. 644-648 (1975).

Baken, R. and Orlikoff, R., Clinical Measurement of Speech and Voice, $2^{nd}$ Ed., Singular Publishing (2000).

Rothenberg, M. A new inverse-filtering technique for deriving the glottal air flow waveform during voicing *J. of the Acoustic Society of America* 53, pp. 1632-1645 (1973)

Hoffman M. R., Baggott, C. D., and Jiang J., Reliable Time to Estimate Subglottal Pressure, *J. of Voice*. March; 23(2): pp. 169-174 (2009)

The primary energy source for the acoustic energy produced by the human voice is the air pressure in the lungs. This air pressure is sometimes referred to as the tracheal pressure or the subglottal pressure, since in the absence of a strong upper respiratory constriction these three pressures are approximately equal in speech or singing. However, because of the inaccessibility of the lungs, the air pressure in the lungs during speech or singing is difficult to determine clinically. Most previous attempts to directly measure lung pressure during speech have employed highly invasive techniques that are not practical for routine clinical measurements or for speech training exercises, such as the use of a tracheal puncture, in which a hypodermic syringe connected to a system for recording air pressure is inserted between the cartilaginous rings of the trachea (Hertegard, et al. (1995) Though useful for research purposes under appropriate medical supervision, this method would be rejected by most clinicians and patients for routine screening or speech training exercises.

Another invasive technique that has been used for measuring subglottal pressure during speech consists of inserting a miniature pressure transducer through the glottis into the trachea (Kitzing and Löfqvist 1975). In this method, the vocal folds and nearby tissues must be anesthetized to suppress the glottal closure reflex that prevents the potentially fatal aspiration of food or other foreign bodies. The need for anesthetization and the potential complications from placing a foreign body into the subglottal space make this also generally unacceptable for routine screening or speech training.

A non-invasive technique for measuring subglottal pressure during speech according to the previous art involves placing the subject in a hard walled chamber called a plethysmograph, with an airtight seal at the neck. The variations in air pressure in the chamber reflect to some extent the compression of lung air, and a number of attempts have been made to deduce the variation of subglottal pressure from the chamber pressure. However, the plethysmograph method is problematic enough that it is rarely used [Baken and Orlikoff, 2000]. That the plethysmograph method has been used at all is testament to the importance of noninvasive measurement of lung pressure in understanding vocal function in speech.

A fourth technique for measuring the subglottal pressure according to the previous art involves interrupting the supraglottal airway during the voice production with a fast acting valve, for example a valve termed a balloon valve, and recording the air pressure just behind the valve. (Hoffman et al., 2009) According to the measurements of Hoffman, et al. (2009), after about 150 ms this pre-valve pressure has equalized with the subglottal pressure for a variety of voice modalities. However, the dependence of this method on the use by the subject of a voice mode that is not overly adducted as well as the acoustic distortion of the speech caused by a mechanical valve assembly near the lips, make this method unacceptable for routine screening or speech training.

In 1973, the applicant introduced the concept of estimating subglottal pressure during speech by recording the peak intraoral air pressure during unvoiced bilabial consonants (as /p/ in English) and using an interpolation algorithm to estimate the lung pressure between the consonants (M. Rothenberg, A new inverse-filtering technique for deriving the glottal air flow waveform during voicing Journal of the Acoustic Society of America, Vol. 53, 1632-1645). This method is based on the fact that if the outlets of the oral chamber are closed for producing the bilabial plosive (lips and velopharyngeal passage both closed), and the glottis is open for the articulation of the unvoiced consonant, the intraoral pressure will equalize with the tracheal pressure in a matter of milliseconds. We will refer to this method as the interpolation technique.

However, the interpolation technique, as implemented according to the previous art, does not provide a real-time measurement; it has been used only for the analysis of previously recorded speech or singing, using a digital computer to implement the interpolation algorithm. One result of this limitation is that the interpolation technique as implemented according to the previous art could not be used for biofeedback in voice training exercises. In addition, the technique implemented according to the previous art is cumbersome when used in routine speech testing.

The present application is for a method and device that will apply a version of the interpolation technique for subglottal pressure estimation from intraoral air pressure during speech or singing in essentially real-time by using real-time low-pass filtering and a peak-hold system that holds a measured peak value for a period of time sufficient for observation.

SUMMARY

It an object of this invention to extend the interpolation technique for estimating subglottal pressure during speech from the intraoral air pressure, as described by the inventor in Rothenberg 1973, to making real-time measurements of subglottal pressure suitable for use in medical screening and in speech training exercises. This is accomplished by using real-time low-pass filtering of the intraoral pressure signal and using a peak detection and extrapolation means that holds the filtered pressure signal peak for a period of time sufficient to allow its observation.

DRAWINGS—FIGURES

FIG. 1 Block diagram of a system for subglottal measurement and display during speech.

Figure 2:
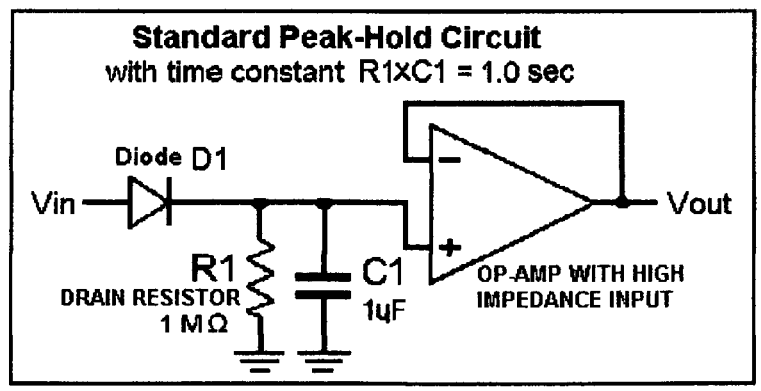

FIG. 2 Electrical circuit diagram for a standard peak-hold circuit.

Figure 3:
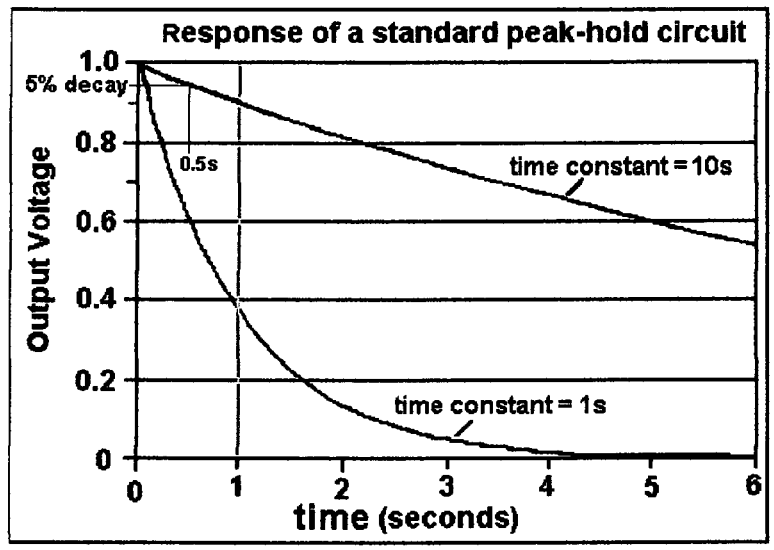

FIG. 3 Chart showing the time response of a standard peak-hold circuit to a negative step in the input of magnitude one, going from one volt to zero volts at t=0.

Figure 4:
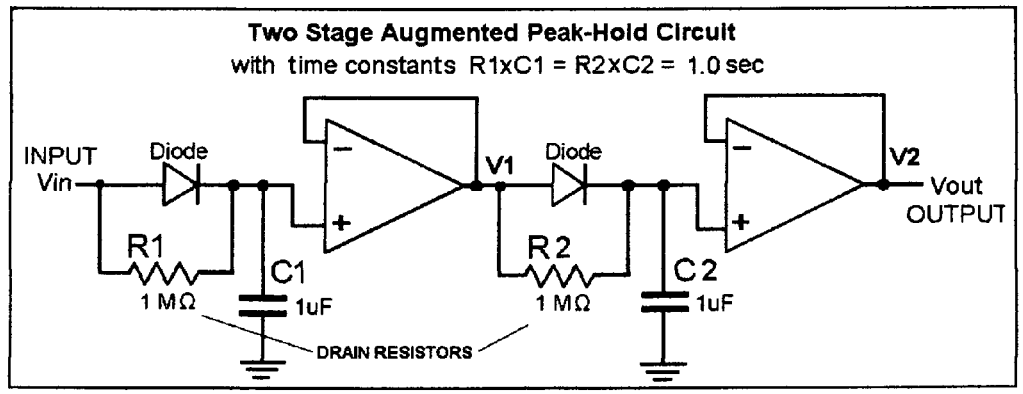

FIG. 4 An electrical circuit diagram for an augmented peak-hold circuit described in this application having two stages, with a time constant of one second in each stage.

Figure 5:
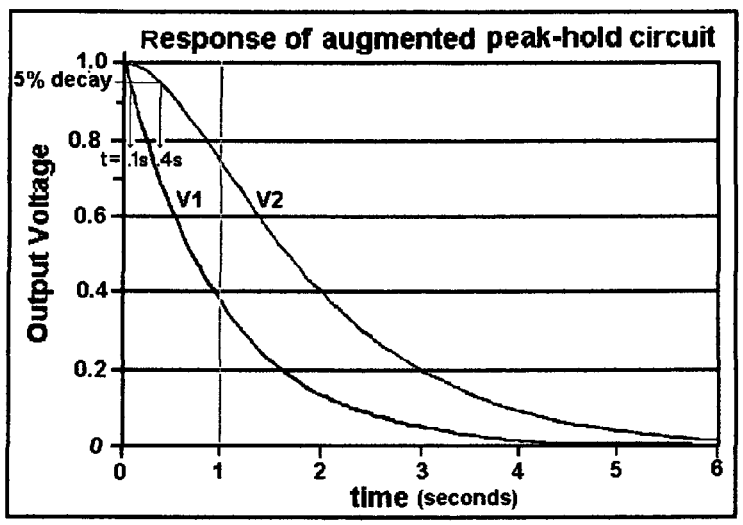

FIG. 5 Chart showing the response at Vout of the circuit in FIG. 4 to a negative step in the input of magnitude one, going from one volt to zero volts at t=0.

Figure 6:
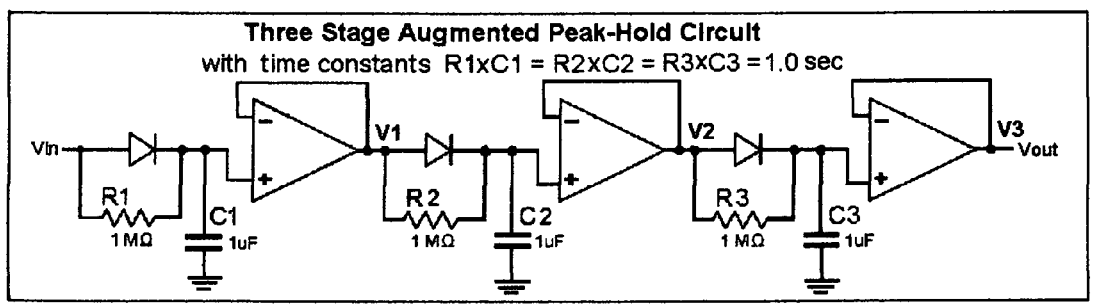

FIG. 6 An electrical circuit diagram for an augmented peak-hold circuit described in this application having three stages, with a time constant of one second in each stage.

Figure 7:
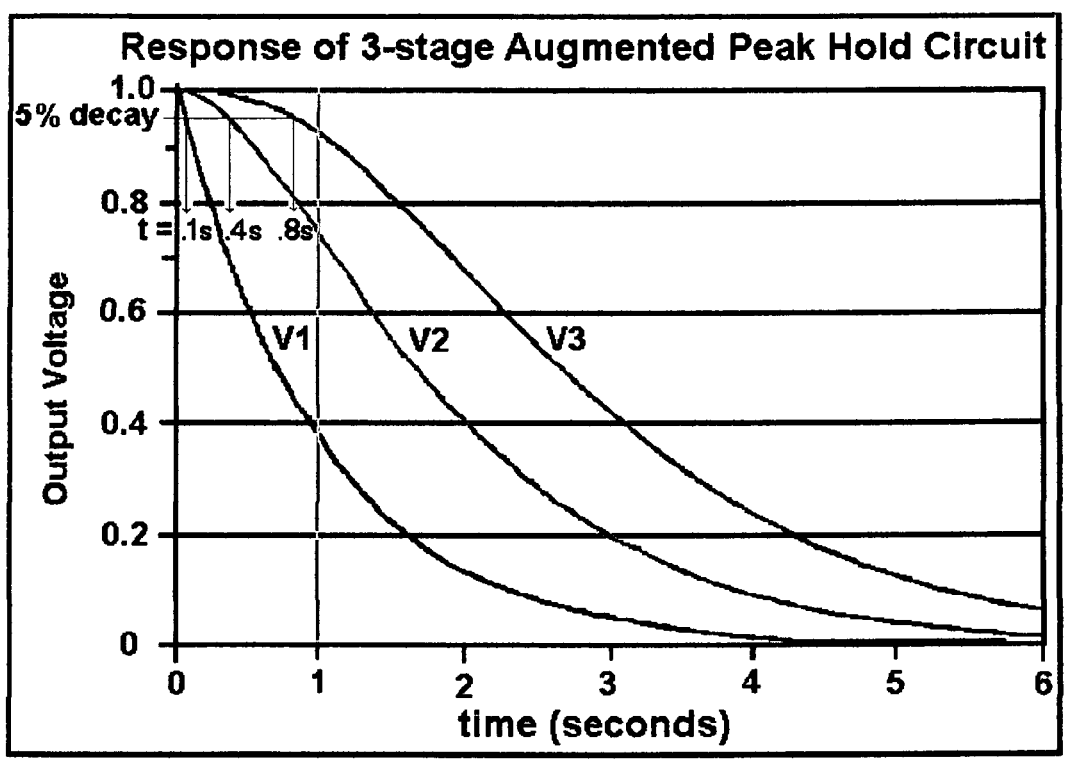

FIG. 7 Chart showing the response at Vout of the circuit in FIG. 6 to a negative step in the input of magnitude one, going from one volt to zero volts at t=0.

Figure 8:
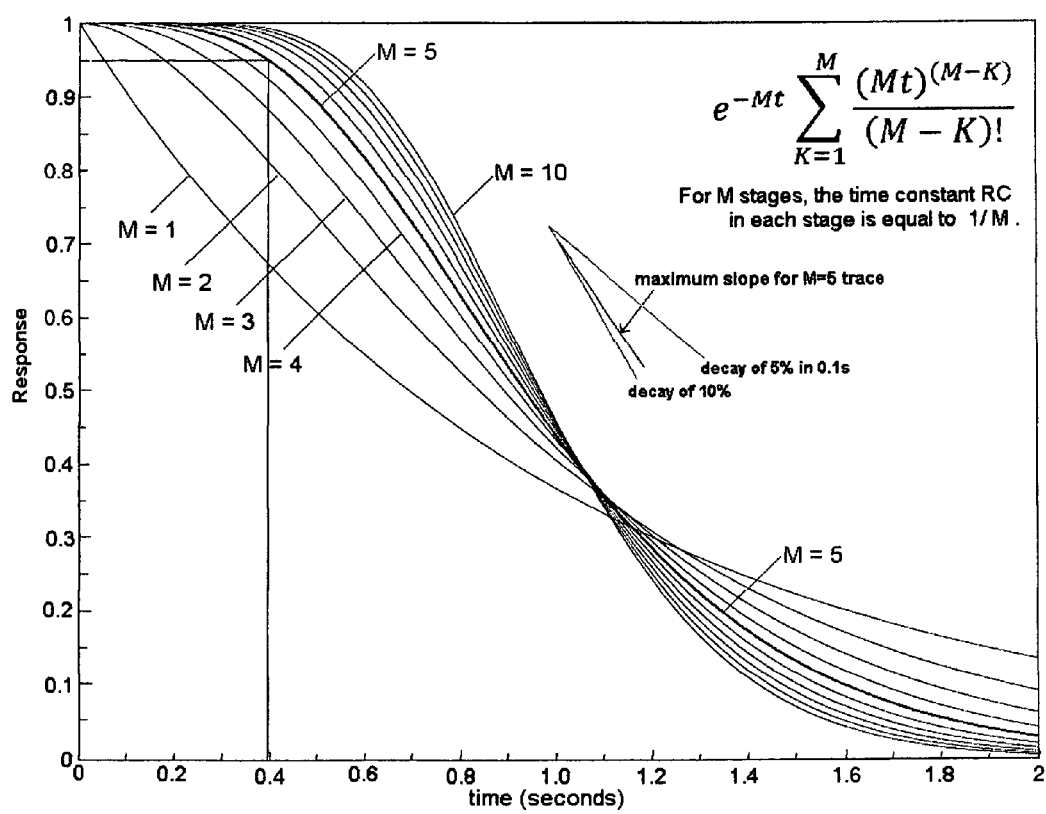

FIG. 8 Chart showing the responses to a negative step in the input of magnitude one at t=0, going from one volt to zero volts, at Vout of an augmented peak-hold circuit such as that in FIG. 6 but having M stages, with M going from 1 to 10, with the time constant in each stage equal to 1/M.

DETAILED DESCRIPTION OF THE PREFERRED EMBODIMENTS

In the method and device described in this application, a tube 1 with a small diameter, nominally a few millimeters, is inserted into the oral chamber of the subject's vocal tract, nominally through the lips at the corner of the mouth, so that the tube senses the intraoral air pressure when the lips are closed.

The sensing tube is connected to a pressure transducer and preamplifier 2 having a range commensurate with the lung pressures being measured. The output of the transducer and preamplifier is input to a low-pass filter 3 that essentially removes the speech acoustic energy, that is, the energy above about 40 Hz.

The output of the low pass filter is input to a system 4 for detecting the peak value during each intraoral pressure pulse that occurs during an unvoiced bilabial stop consonant. The system 4 must be designed to also hold the last peak value for a period long enough to enable a reading of the value of the peak and decay thereafter in a matter of seconds.

From experiments with natural speech, performed by the inventor, a hold time of approximately 0.5 second is suggested. In the absence of additional intraoral pressure peaks after the hold period, in order to allow future pressure peaks to be accepted if they are lower than the previous peak, the output of peak detection and hold system 4 should decay at a rate such that the output decays to at least half its peak value in not more than a second. We will call this the terminal decay. This degree of terminal decay would be accomplished by an average rate of terminal decay, after the hold time, of approximately 5% in 0.1 seconds.

Finally, the output of peak detection and hold system 4 is sent to a display or recording means 5, which may be an analog meter, a digital meter, or an array of LED lights. The indicating means in 5 may be augmented by a recording means to preserve the output of the peak detection and hold system 4 for future reference.

The peak detection and hold system 4 could be implemented by a suitably programmed microprocessor; however, a suitable analog electrical circuit devised by the inventor for this purpose is described below. It is envisioned that the analog circuit described in this application would be more economical to produce than a microprocessor version, and so keep down the cost of the device. On the other hand, a microprocessor version of the peak detection and hold system 4 could be programmed to detect and measure a number more than one of such peaks and perform more complex operations involving such peaks, such as averaging or interpolation.

Derivation of the Analog Peak Detection and Extrapolation Circuit

Though there are many forms of peak-hold analog circuits disclosed in the literature, perhaps the simplest and most basic simple peak-hold circuit is shown in the FIG. 2 with some typical circuit values. The diode D1 charges the capacitor C1 to a local peak of Vin, providing the capacitor voltage is not already greater than such peak.

C1 then discharges through the 'drain resistor' R, with the voltage on C1 decaying exponentially. Assuming a perfect op-amp and diode, the decay in capacitance voltage is exponential with time constant R1×C1, as long as the input to the diode Vin is never larger than the capacitance voltage. The output voltage resulting from an input peak of 1.0 followed by a sharp decay to zero (a negative step function going from 1 to 0) is shown in FIG. 3 for two values of the time constant R1×C1. The value of 10 for the longer time constant was chosen as the approximate minimum required to meet our 5% decay criterion for hold time. Note, however, that if the time constant is chosen to meet the 5% criterion, i.e., R1×C1 is equal to or greater than 10 seconds, then the terminal decay time may be too great. More precisely, a circuit with a time constant of 10 seconds will take 10 seconds to decay to 1/e=0.37).

To solve the problem of a conflict between the desired hold time and the desired terminal decay time, this application presents a modification of a standard peak-hold circuit in which the drain resistor is returned to voltage input to the diode instead of to ground, as are R1 and R2 in FIG. 4.

We will refer to such a circuit as an augmented peak-hold circuit, or AP-H. Using an augmented peak-hold circuit slows the initial discharge of the capacitor C2, thus creating a period in which the output is held near the peak value.

Let us assume that a hold in the decay is marked by a decay of less than 5%. In FIG. 5 it can be seen that by adding an AP-H stage with the same time constant as the first stage, the decay period is increased from approximately 0.1 s to 0.4 s, a fourfold increase, while increasing the terminal decay time by less than a factor of two.

It should be noted that cascading two stages of the standard peak-hold circuit in FIG. 2 would have no such effect, though a roughly similar effect may be obtained by adding an inductance in series with R1 of the standard sample hold circuit.

The time that the peak voltage is held (stays within approximately 95% of the initial peak) can be further increased by using an additional stage of AP-H, as in FIG. 6.

The operation of the circuit in FIG. 6 is illustrated in FIG. 7. The curves in the chart of FIG. 7 show the voltage at the outputs of the three stages, referred to as V1, V2 and V3 respectively, after the input Vin leaves its peak value and goes quickly to zero (a negative step function).

FIG. 7 shows that with three AP-H sections, and with all sections having the same unity time constant, the output is still at over 95% of the peak value after 0.8 seconds (rounded to one significant figure). This is a reasonable value for real-time observation; however, the extension of the hold time can be further increased with more sections cascaded. In fact, it can be shown mathematically that the response of M cascaded sections, all having a time constant of one second, to an input with a value of one unit that drops quickly to zero, is given by the following expression in Equation 1, where equation 1 represents the response of a filter having M stages with the time constant for each respective stage equal to 1, to a negative step of unity amplitude (voltage going from 1 to 0 at=0).

$$e^{-t} \sum_{K=1}^{M} \frac{t^{(M-K)}}{(M-K)!}$$ Equation 1

As can be seen in FIG. 7, as cascaded stages are added having the same time constant, the delay caused by the filter increases approximately in proportion to the number of stages.

This undesirable result of adding cascaded stages can be compensated for by using a time constant that varies inversely with the number of stages in the filter. For example, if the time constant for a single stage filter is assumed to be one second, then the time constant for each stage of an M-stage filter would then be 1/M. The response expression in Equation 1 then would be as follows in Equation 2, where Equation 2 represents the response of an M-stage filter to a negative step of unity amplitude (voltage going from 1 to 0 at t=0) for M stages, with the time constant for each respective stage equal to 1/M.

$$e^{-Mt} \sum_{K=1}^{M} \frac{(Mt)^{(M-K)}}{(M-K)!}$$ Equation 2

In FIG. 8, the responses of the filters in Equation 2 are plotted for M equal one to ten. We will look more closely at the case of M=5, as a practical compromise between complexity and performance.

FIG. 8 shows that according to our 95% decay criterion, a 5-stage cascaded AP-H circuit, with time constants equal to 1/M=⅕ second would have a delay of approximately 0.4 seconds, while having a final decay to a third of its peak value in approximately 1.1 seconds. The maximum decay rate can be estimated from the graph to be approximately 9.5% in 0.1 second, and the average decay rate after the hold period is roughly half of that. These figures show that 4 or 5-stage APH circuit would fit our experimentally determined criteria, and this conclusion has been confirmed by tests using a 4-stage APH circuit, though the optimal number of stages and the optimal values of the RC time constants in each stage should be determined by further testing.

The method and system may, of course, may be carried out in specific ways other than those set forth without departing from the spirit and essential characteristics of the invention. Therefore the presented embodiments should be considered in all respects as illustrative and not restrictive, and all modifications falling within the meaning and equivalency range of the appended claims are intended to be embraced therein. For example, there are many possible implementations of a standard peak-hold circuit, each of which could be converted to an augmented peak-hold circuit with a plurality of stages for the purpose described in this application. The scope of this patent should not be limited to the example given for a standard peak-hold circuit.

What is claimed is:

1. An apparatus for indicating the air pressure in the lungs during speech or singing comprising:
    a pressure transducer for converting air pressure to an electrical signal;
    a sensing tube for passing the intraoral pressure to said pressure transducer;
    a low pass filter for receiving said electrical signal from said pressure transducer and removing an acoustic energy from the signal;
    a peak detection and holding means for receiving the output of said low pass filter and detecting peak values of the output of the low pass filter and holding said peak values, or an approximation of said peak values, for a period of time;
    a recording or display means for displaying a present value of the output of said peak detection and holding means.

2. An apparatus according to claim 1 in which the peak detection and holding means is a peak-hold electronic circuit having a plurality of stages in which in at least one of the stages the drain resistance is referred to the input of the stage instead of to ground.

3. An apparatus according to claim 1 in which the peak detection and holding means is a microprocessor programmed to perform the hold and decay functions.

4. An apparatus according to claim 3 in which the microprocessor comprising the peak detection and holding means is programmed to record plurality of successive peaks and compute an average of, or interpolation between, the values of such peaks.

5. An apparatus according to claim 1 in which the peak detection and hold means contains a peak-hold electronic circuit in which an inductance is in series with a drain resistor in order to effect a hold period.

* * * * *